US00PP08160P

United States Patent [19]

Dehan

[11] Patent Number: Plant 8,160

[45] Date of Patent: Feb. 23, 1993

[54] ASTER PLANT NAMED SUNJOY

[75] Inventor: Klara Dehan, Holon, Israel

[73] Assignee: Danziger - "Dan" Flower Farm, Post Belt Dagan, Israel

[21] Appl. No.: 687,163

[22] Filed: Apr. 19, 1991

[51] Int. Cl.[5] ..... A01H 5/00

[52] U.S. Cl. ..... Plt./68.1

[58] Field of Search ..... Plt./68, 68.1

*Primary Examiner*—James R. Feyrer

*Attorney, Agent, or Firm*—Foley & Lardner

[57] ABSTRACT

An aster plant named Sunjoy particularly characterized by its single flower type; long and narrow petals of medium violet color; and its vigorous, highly vegetative growth habit with extensive secondary branching.

1 Drawing Sheet

The present invention comprises a new and distinct cultivar of aster hybrid, hereinafter referred to by the cultivar name Sunjoy.

The new cultivar was originated from a cross made by applicant in a controlled breeding program in Mishmar Hashiva, Israel. The female, or seed, parent was a cultivar designated 2-P1. The male, or pollen, parent was a cultivar designated 35-P-3. Both parents are hybrids of aster cultivars, species unknown.

Sunjoy was discovered and selected by applicant as a flowering plant within the progeny of the stated cross in a controlled environment in Mishmar Hashiva, Israel. Asexual reproduction of the new cultivar by vegetative cuttings, as performed by applicant at Mishmar Hashiva, Israel, has demonstrated that the combintion of characteristics as herein disclosed for the new cultivar are firmly fixed and retained through successive generations of asexual reproduction.

Sunjoy has not been observed under all possible environmental conditions. The phenotype may vary significantly with variations in environment such as temperature, light intensity and day length, without however any variance in geneotype. The following observations, measurements and comparisons describe plants grown in Mishmar Hashiva, Israel under conditions which closely approximate those generally used in commercial practice.

The following traits have been repeatedly observed and are determined to be basic characteristics of Sunjoy which, in combination, distinguish this Aster as a new and distinct cultivar:

1. Single flower type.
2. Petals are very narrow and approximately 30 in number. In several instances there are spaces between the petals which create a different appearance.
3. The petal color is a unique medium violet.
4. Excellent growth habit, developing many branches and stems. The total number of flowers produced on secondary branches depends on the season, with the number of buds in the summer being higher than in the winter.

The combined characteristics of the new cultivar are sufficiently unique that no meaningful comparison can be made based on other cultivars familiar to applicant. The female parent is primarily characterized by its many stems and light purple petal color. The male parent also produced many stems and has a light pink flower color. Based on the characteristics of the parents, the new cultivar is distinctly different and unexpected.

The accompanying color photographic drawings show a typical specimen plant the new cultivar.

The upper photo is a front elevational view of a section of a flowering plant, and the bottom photo is a closeup of a single flower.

The colors appearing in the photographs do not precisely correspond to the described color values, which are correct.

In the following description, color references are made to The Royal Horticultural Society Colour Chart (R.H.S.), except where general colors of ordinary significance are referred to. Color values were taken under artificial light conditions at approximately noon on Jan. 20, 1991 at Mishmar Hashiva, Israel.

Botanical classification: Aster hybrid cv Sunjoy.

Parentage:

*Male parent.*—35-P-3.

*Female parent.*—2-P1.

Propagation: By stem cuttings, tissue culture and division.

INFLORESCENCE

A. Capitulum:

*Form.*—Daisy, flat.

*Type.*—Single.

*Diameter across face.*—2–2.5 cm.

B. Corolla of ray florets:

*Color (general tonality from a distance of three meters).*—Pink to violet.

*Color (upper surface).*—87C.

*Color (under surface).*—76B.

*Shape.*—Petals are very narrow; approximately 10 mm long and 3 mm wide.

*Total number of ray florets.*—30 on average; in winter conditions with lower temperatures, petal count is normally higher; in higher summer temperatures, petal count will normally be less.

Corolla of disc florets:

*Color (mature).*—Yellow-green 153B.

*Color (immature).*—Yellow 7B.

*Diameter of disc.*—0.7 cm.

D. Reproductive organs:

*Androecium.*—Color yellow 1D.

*Gynoecium.*—Color yellow 1D.

E. Flowering season: Natural flowering in Israel is approximately September 15–20. In photoperiodic production programs, flower response is approximately six weeks of short days following four weeks of long days.

PLANT

A. General Appearance: Vigorous growth habit and extensive secondary branching produces highly vegetative plant. In the first flash after planting, 7–10 branches are produced.

B. Height: At time of first flowering, plant is approximately 90–100 cm in height.

C. Foliage:

*Color.*—137A.

*Shape.*—Very long and narrow; typical leaf measures 14 cm in length and 0.8 cm in width.

I claim:

1. A new and distinct cultivar of aster plant named Sunjoy, as illustrated and described.

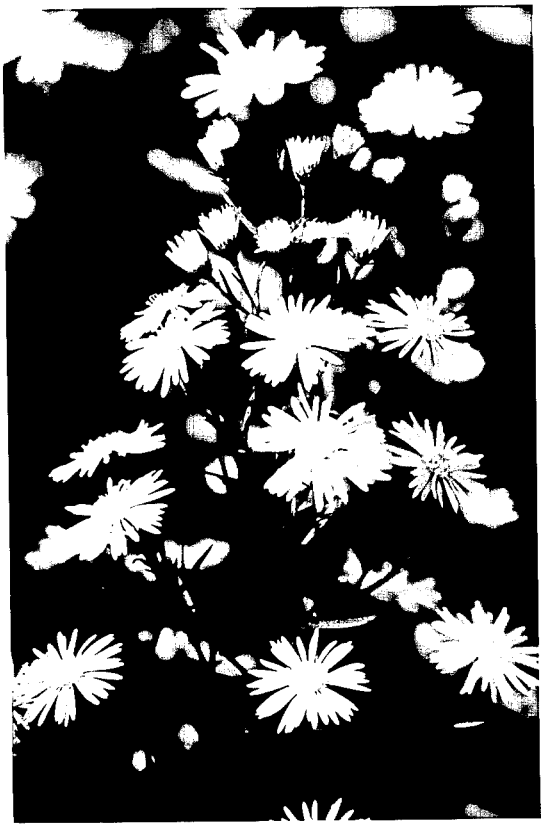
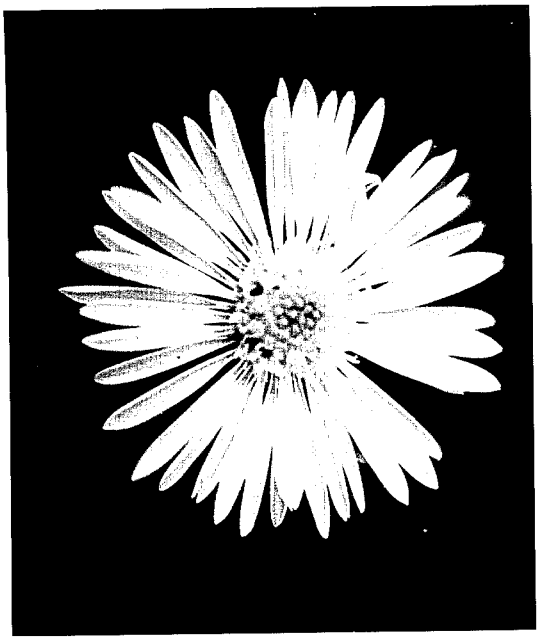

* * * * *